United States Patent [19]

Bernstein

[11] Patent Number: 5,008,289

[45] Date of Patent: Apr. 16, 1991

[54] COMPOSITION FOR TREATING NASAL DISORDERS AND HEADACHES

[75] Inventor: Joel E. Bernstein, Deerfield, Ill.

[73] Assignee: GalenPharma, Inc., Deerfield, Ill.

[21] Appl. No.: 279,586

[22] Filed: Dec. 2, 1988

[51] Int. Cl.$^5$ ..................... A61K 31/24; A61K 31/16
[52] U.S. Cl. .................................. 514/535; 514/626; 514/627
[58] Field of Search ....................... 514/159, 626, 627; 424/443

[56] References Cited

U.S. PATENT DOCUMENTS

| | | | |
|---|---|---|---|
| 4,466,973 | 8/1984 | Rennie | 514/626 |
| 4,537,776 | 8/1985 | Cooper | 514/424 |
| 4,557,934 | 12/1985 | Cooper | 514/159 |
| 4,801,458 | 1/1989 | Hidaka et al. | 424/443 |

OTHER PUBLICATIONS

Chemical Abstracts (vol. 108): 181892; (1988).

*Primary Examiner*—Stanley J. Friedman
*Assistant Examiner*—Kevin E. Weddington
*Attorney, Agent, or Firm*—Jones, Day, Reavis & Pogue

[57] ABSTRACT

Compositions and methods for treating the symptoms of certain allergy-related conditions using capsaicin in solution or suspension combined with a selected local anesthetic, topical steroid or antihistamine. The same methods and compositions may be used to treat headaches.

7 Claims, No Drawings

COMPOSITION FOR TREATING NASAL DISORDERS AND HEADACHES

BACKGROUND OF THE INVENTION

Capsaicin is a chemical isolated from the fruits of plants of the nightshade family, principally the pepper plant. It requires processing of about 10,000 pounds of peppers to extract a yield of 1 pound of capsaicin. Capsaicin has in recent years been used topically on the skin to treat psoriasis and to relieve certain types of superficial pain.

Ground pepper, containing capsaicin, has long been utilized by magicians and tricksters as "sneezing powder". It affects the nose and airway passages of the respitory system by causing intense irritation, producing vigorous sneezing and coughing and, if exposure is extreme, shortness of breath. Additionally, direct exposure of pepper to the mucosa of the nose may result in intense local pain, and not uncommonly, severe headache.

It has been discovered that capsaicin, when applied repeatedly locally to the nasal mucosa or directed to the respiratory passages can produce quite contrary and surprising effects.

In particular, it has been found that capsaicin has beneficial effects in treating the symptoms of vasomotor rhinitis, commonly encountered throughout the year, and allergic rhinitis encountered during the ragweed and mold season. It was noticed that a person suffering from these conditions, while working with capsaicin powder, inhaled relatively large amounts of the powder over a several day period, causing intense burning pain and sneezing. This was followed several hours later by an intense headache involving the tempero-frontal areas. On the second day of exposure to the powder, the foregoing symptoms were similar, but less intense. After four days of exposure, the subject no longer experienced the intense nasal pain, sneezing, or headache, but noticed that congestion from vasomotor rhinitis was no longer apparent. Indeed for the next few days, the subject experienced substantially less of his usual seasonal nasal discomfort.

On the basis of these results, solutions of capsaicin were prepared for introduction into the nose to treat allergic and other inflammatory disorders of the nose as well as to prevent or treat headaches. In introducing such drops into the nasal passages of several test subjects it was discovered that the capsaicin drops could produce intense almost unbearable pain in the naive patient. Several types of other agents were then incorporated into the formulation along with the capsaicin to relieve this adverse reaction to the capsaicin nose drops. In the course of trying to reduce this adverse capsaicin effect, the topical anesthetics lidocaine (Entry 5310, p. 786, *Merck Index*, Tenth Edition 1983) and benzocaine (ethyl aminobenzoate, Entry 3710, p. 546, *Merck Index*, Tenth Edition 1983) the topical steroids hydrocortisone and betamethasone valerate and the histamine blockers diphenhydramine, doxepin and amitriptyline were used.

It was discovered that the topical anesthetics lidocaine and benzocaine, in concentrations of from about 0.5% to about 20% were most effective in preventing the intense burning pain of the nasal mucosa induced by capsaicin. Topical steriods and anihistamines appeared to reduce the burning effects of capsaicin, but to a lesser degree than the anesthetics.

DETAILED DESCRIPTION OF THE INVENTION

In the practice of this invention nose drops are prepared by introducing capsaicin into a pharmaceutically acceptable carrier in concentrations from about 0.001% to about 1.0% by weight, and the resulting composition is used to treat or prevent inflammations of the nose (such as from allergic rhinitis; as well as to treat or prevent severe recurring headaches. Because these drops may produce initial pain of an unbearable type, in the preferred practice of this invention, from about 0.5% to about 20% by weight of a topical anesthetic such as lidocaine or benzocaine are included in the preparation to reduce the intial discomfort that the capsaicin drops may produce. Corticosteroids, such as hydrocortisone or betamethasone valerate or antihistamines such as doxepin or diphenhydramine may also be incorporated into the nasal drops to reduce the symptoms of discomfort produced, with the corticosteroids being present in concentrations of about 0.05% to about 5.0%.

Use of this invention is illustrated by the following examples.

EXAMPLE 1

A 44 year old male with allergic rhinitis and accompanying headaches was treated with a nasal solution containing 0.025% capsaicin. The nasal solution was instilled four times daily. On the first 2 days introduction of the nasal solutions produced burning pain and sneezing. However, after 3 days these effects diminished and after 7 days of continued capsaicin application to the nasal passages, the patient no longer experienced episodes of nasal congestion, sneezing, or headaches.

EXAMPLE 2

The 44 year old patient described in Example 1 was treated with a nasal solution containing 0.025% capsaicin and 10% lidocaine. This solution produced similar relief of the patient's symptoms as in Example 1 above, with only mild nasal discomfort during the first few days of capsaicin application.

While the foregoing has presented certain specific embodiments of the invention, it is to be understood that such have been made by way of example only and are not intended to limit the scope of the invention as herein described and claimed. It is expected that others will perceive variations which, while differing from the foregoing, do not depart from the spirit and scope of the invention.

I claim:

1. A composition for treating the symptoms of nasal disorders and headaches, said composition comprising:
    a solution or suspension formulated from a pharmaceutically acceptable carrier for instillation into the nose, said solution or suspension containing capsaicin in concentrations from about 0.001% to about 1% weight
    and including a pharmaceutically acceptable local anesthetic selected from the group consisting of lidocaine or benzocaine in concentrations from about 0.5% to about 20% by weight.

2. The composition of claim 1 including a topical steroid.

3. The composition claim 1 including a topical antihistamine.

4. The composition of claim 2, wherein said topical steroid is hydrocortisone in concentrations from about 1.0% to about 5.0% by weight.

5. The composition of claim 2 wherein said topical steroid is betamethasone valerate in concentrations from about 0.05% to about 0.2% by weight.

6. The composition of claim 3 wherein said topical antihistamine is doxepin in concentrations from about 1.0% to about 5.0% by weight.

7. The composition of claim 3 wherein said topical antihistamine is diphenhydramine in concentrations of from about 5.0% to about 10.0% by weight.

* * * * *